United States Patent [19]

Nalelwajek et al.

[11] Patent Number: 4,847,442

[45] Date of Patent: Jul. 11, 1989

[54] PROCESS FOR THE PREPARATION OF DIFLUOROBENZENES

[75] Inventors: David Nalewajek, West Seneca; Michael Van Der Puy, Cheektowaga, both of N.Y.

[73] Assignee: Allied-Signal Inc., Morris Township, Morris County, N.J.

[21] Appl. No.: 220,862

[22] Filed: Jul. 18, 1988

[51] Int. Cl.$^4$ .................. C07C 17/24; C07C 17/33; C07C 21/24

[52] U.S. Cl. ................................................ 570/142

[58] Field of Search ............................. 570/143, 142

[56] References Cited

U.S. PATENT DOCUMENTS

| | | | |
|---|---|---|---|
| 2,746,997 | 5/1956 | Reid et al. | 570/142 |
| 3,018,306 | 1/1962 | Sweeney et al. | 570/142 |
| 3,221,069 | 11/1965 | Bain et al. | 570/143 |
| 3,240,792 | 3/1966 | Patrick et al. | 570/143 |
| 3,386,899 | 6/1968 | Shepard et al. | 204/59 |
| 3,501,541 | 3/1970 | Dubeck et al. | 570/142 |
| 3,555,100 | 1/1971 | Garth et al. | 570/142 |
| 3,816,409 | 6/1974 | Bauer et al. | 260/239.3 B |
| 4,031,221 | 6/1977 | Helsley et al. | 424/267 |
| 4,075,252 | 2/1978 | Boudakian | 260/649 F |
| 4,096,196 | 6/1978 | Boudakian | 260/650 F |
| 4,152,356 | 5/1979 | Kim | 570/143 |
| 4,351,962 | 9/1982 | Gradeff et al. | 568/432 |

FOREIGN PATENT DOCUMENTS

| | | | |
|---|---|---|---|
| 1030336 | 5/1958 | Fed. Rep. of Germany | 570/142 |
| 0265854 | 5/1988 | Fed. Rep. of Germany | |
| 43130 | 3/1986 | Japan | 570/142 |
| 970746 | 9/1964 | United Kingdom | 570/143 |
| 1130263 | 10/1968 | United Kingdom | |
| 2122190 | 1/1984 | United Kingdom | 570/143 |

OTHER PUBLICATIONS

Hawthorne et al., "J. Org. Chem.", vol. 25 (1960), pp. 2215 and 2216.
Balz et al., Ber. 60, 1186 (1927), No translation.
Schiemann et al., Ber. 62, 3035 (1929), No translation.
Chem. Abs. 54, 5518c (1960).
Chem. Abs. 56, 3408g (1962).
Schiemann et al., Ber. 98, 3410 (1965), No translation.
Chem. Abs. 71, 80903a (1969).
Chem. Abs. 76, 112801n (1972).
Vasek et al., J. Fluorine Chem. 2, 257 (1972/73).
Shiley et al., J. Fluorine Chem. 2, 19(1972/73).
Vasek et al., J. Fluorine Chem. 3, 397 (1973/74).
Hartman et al., J. Org. Chem. 42(8), 1468 (1977).
Chem. Abs. 104, 109476b (1986).

*Primary Examiner*—J. E. Evans
*Attorney, Agent, or Firm*—Melanie L. Brown; Jay P. Friedenson

[57] ABSTRACT

Difluorobenzene is prepared by a multistep process involving fluorination of dichlorobenzoyl chloride to provide difluorobenzoyl fluoride, conversion thereof to difluorobenzoyl chloride, hydrogenation of this to difluorobenzaldehyde and decarbonylation of the aldehyde to difluorobenzene.

19 Claims, No Drawings

PROCESS FOR THE PREPARATION OF DIFLUOROBENZENES

BACKGROUND OF THE INVENTION

The present invention relates to a process for the preparation of difluorobenzenes.

Fluorobenzene is produced by processes such as diazotization of aniline using $NaNO_2$ in HF followed by decomposition as taught by Chem. Abs. 104, 109476b (1986); gas phase reaction of fluorine and benzene as taught by Chem. Abs. 76, 112801n (1972); and pyrolysis of mixtures of dienes and fluorochloromethanes as taught by Chem. Abs. 71, 80903a (1969).

The main process for production of meta- or of arene diazonium tetrafluoroborates as taught by Balz et al, Ber. 60, 1186 (1927). 1,3-difluorobenzene is based on the thermal decomposition al, Ber. 60, 1186 (1927). The first step of the process involves the preparation and isolation of a dry diazonium fluoroborate while the second step deals with the controlled decomposition of the salt by heat to yield an aromatic fluoride, nitogen, and boron trifluoride. According to Schiemann et al., Ber. 62, 3035 (1929), 1,3-difluorobenzene was prepared in 31% yield from the bis-diazonium salt derived from m-phenylenediamine. See also Roe, Organic Reactions 5, 193(1949) and Suschitzky, Advances in Fluorine Chemistry 4, 1(1965) for detailed analyses of the Balz-Schiemann Reaction.

In attempts to improve yields and facilitate product recovery, modifications of the Balz-Schiemann reaction as applied to the synthesis of 1,3-difluorobenzene have appeared over the years. Chem. Abs. 54, 5518c (1960) discloses the thermal decomposition of various haloaniline fluoroborate salts to fluorobenzenes. The process requires multiple steps including the preparation of the haloanilines and their subsequent diazotization, isolation, and decomposition. Based on the last step, 1,3-difluorobenzene was prepared in a 57% yield.

Chem. Abs. 56, 3408 g (1962) teaches the diazotization of meta-phenylenediamine in sulfuric/glacial acetic acid and subsequent treatment with $HBF_4$. The dried diazonium salt was decomposed thermally in small portions at 210° C. to yield 45% 1,3-difluorobenzene.

According to Hartman et al., "Crown Ether-Copper-Catalyzed Decomposition of Arenediazonium Fluoroborates," J. Org. Chem. 42(8), 1468 (1977), 2,4-difluorobenzenediazonium tetrafluoroborate was decomposed in methylene chloride under a nitrogen atmosphere in the presence of catalytic amounts (10 mol %) of dicyclohexyl-18-crown-6(1) and powdered copper for 15 minutes at 40° C. to yield 1,3-difluorobenzene in 95% yield. The Hartman et al. process is disadvantageous because the process requires isolation of the diazonium salt, uses toxic and expensive crown ethers which have to be recovered or recycled, and uses starting materials which are not commercially available. The reported yields are not isolated but are based on GC analysis.

U.S. Pat. No. 4,075,252 discloses a process wherein a suitable amine substrate is diazotized with a diazotization agent in hydrogen fluoride to form the corresponding diazonium fluoride. This diazonium fluoride is thermally decomposed to form the aryl fluoride. The Examples teach that using 3-fluoroaniline as a starting material, the yields for 1,3-difluorobenzene were on the order of 46% for the two-step process. This approach is economically unattractive as an industrial process because 3-fluoroaniline is unavailable in commercial quantities.

U.S. Pat. No. 4,096,196 is an improvement on U.S. Pat. No. 4,075,252 in that the diazotization/fluorination is conducted in a hydrogen fluoride medium containing tertiary amine compounds. The Examples teach that using 3-fluoroaniline as a starting material, the yields for 1,3-difluorobenzene were on the order of 70%. Again, such an approach is economically unattractive as an industrial process because 3-fluoroaniline is unavailable in commercial quantities.

In the Balz-Schiemann Reaction, isolation and controlled decomposition of diazonium fluoroborates or diazonium fluorides are troublesome synthetic procedures, particularly on a large scale and repeated nitrations and reductions are necessary to substitute more than one fluorine on the aromatic substrate. The process is also complicated by side reactions which occur during the diazotization or the decomposition stage and which result in the formation of tars, unexpected replacement of the diazonium group by hydrogen, or unwanted displacement of fluorine by ancillary halides usually present as a contaminant in the diazonium salt. These occurrences result in decreased yields of 1,3-difluorobenzene and purification difficulties.

Alternative processes to the Balz-Schiemann reaction have been investigated but with little success. Gunther et al, Ber. 98 3410 (1965) teach the continuous gas phase fluorination of benzene or fluorobenzene with chlorine trifluoride/nitrogen gas mixtures; yields of 1,3-difluorobenzene were on the order of 4%. Other processes include heating mixtures of butadiene and $CHF_2Cl$ at 650° which produced a mixture of 48% ortho-, meta-, and para-difluorobenzenes according to UK Pat. No. 1,130,263; reacting trichlorobenzenes with potassium fluoride or potassium fluoride-cesium fluoride mixtures in dimethylsuflone which produced 1,3-difluorobenzene as a by-product in low yields of about 2 to 4% according to Shiley et al, "Fluorination of 1,2,3-; 1,2,4-; and 1,3,5-Trihalobenzenes with Potassium Fluoride in Dimethyl Sulfone," J. Fluorine Chem. 2, 19 (1972); reacting atomic fluorine with bromobenzene vapor which produced 1,3-difluorobenzene as a by-produce in low yields according to Vasek et al, "Radio frequency Fluorination of Bromobenzene using Elemental Fluorine," J. Fluorine Chem. 2, 257 (1972); and reacting atomic fluorine with fluorobenzene under cold plasma which produced 1,3-difluorobenzene in low yields according to Vasek et al, "The Reaction of Atomic Fluorine with Fluorobenzene," J. Fluorine Chem. 3, 397 (1973).

According to Sams et al, "Molecular Sieve Fluorination of Fluorobenzene Using Elemental Fluorine," J. Org. Chem. 43(11), 2273 (1978), attempts were made to prepare 1,3-difluorobenzene using a molecular sieve fluorination technique. Fluorination of monofluorobenzene resulted in the isolation of various isomers of difluorobenzene in 19% yield; the highest reported yield for the meta isomer was 1.2%.

Difluorobenzenes are employed as chemical intermediates in a variety of applications including pharmaceutical and agricultural. For example, 1,3-difluorobenzene is used in the preparation of Diflunisal (trademark), an anti-inflammatory agent, or in Diflubenzuron (trademark), a potential insecticide. Benzodiazepinones are prepared by reacting 1,2- or 1,4-difluorobenzene in a multistep procedure to yield compounds which exhibit sedative and/or anticonvulsant activity; see U.S. Pat. Nos. 3,816,409 and 4,031,221. Fluorobenzene may also be polymerized to produce products which exhibit good thermal resistance or electrical insulation properties and may also be deposited on other types of polymers to modify their surface characteristics as in U.S. Pat. No. 3,386,899. Because difluorobenzenes are so commercially useful, a simple process for the preparation of difluorobenzenes in good yields is needed.

SUMMARY OF THE INVENTION

The present invention provides a process for the preparation of difluorobenzenes. The process comprises the steps of:

(a) heating a chlorinated benzoyl chloride of the Formula (I)

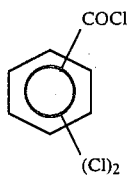

wherein each of the chlorines is independently ortho or para to the —COCl group with potassium fluoride and solvent for the chlorinated benzoyl chloride and the potassium fluoride for a time and at a temperature sufficient to provide a fluorinated benzoyl fluoride of the Formula (II)

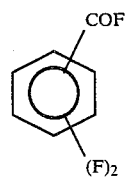

(b) reacting the fluorinated benzoyl fluoride with Lewis acid chloride under conditions and for a time sufficient to provide a fluorinated benzoyl chloride of the Formula (III)

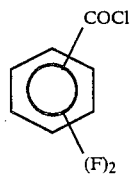

and removing inorganic salts from the reaction medium, (c) reducing the fluorinated benzoyl chloride with hydrogen gas in the presence of a catalyst under conditions and for a time sufficient to provide a fluorinated benzaldehyde of the Formula (IV)

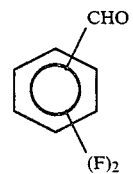

(d) and heating the fluorinated benzaldehyde in the presence of a catalyst for a time sufficient to provide a fluorinated benzene of the Formula (V)

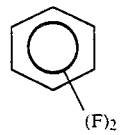

The present process uses commercially available raw materials, allows for ease of separation of difluorobenzenes, and provides good yields of difluorobenzenes. As mentioned earlier, the Balz-Schiemann process limitations include the troublesome isolation and controlled decomposition of diazonium fluoroborates, repeated nitrations and reductions in order to substitute more than one fluorine on the aromatic compound, and side reactions which occur during the diazotization or decomposition stage. These limitations are overcome by the present process. As such, the present invention provides an improved process for the preparation of difluorobenzenes.

Other advantages of the present invention will become apparent from the following description and appended claims.

DETAILED DESCRIPTION OF THE PREFERRED EMBODIMENTS

For the process of the present invention, the starting material for step (a) is a chlorinated benzoyl chloride of the Formula (I) above. Illustrative chlorinated benzoyl chlorides are 2,4-dichlorobenzoylchloride; and 2,6-dichlorobenzoylchloride. Most of these compounds are available in commercial quantities; otherwise, the compounds may be prepared by any known method such as partial hydrolysis of dichlorobenzotrichloride; chlorination of dichlorobenzaldehyde; and reaction of dichlorobenzoic acid and $PCl_5$, phosgene, or $SOCl_2$.

The present process excludes chlorinated benzoyl chlorides of Formula (I) wherein chlorine is meta to the acid chloride group because this compound requires extremely long reaction times or is unreactive. If reaction does occur, the time and temperature required to effect transformation result in decomposition of the fluorinated benzoyl fluoride.

The chlorinated benzoyl chloride of Formula (I) above is heated with potassium fluoride and solvent for the chlorinated benzoyl chloride and the potassium fluoride for a time sufficient to provide a fluorinated benzoyl fluoride of Formula (II) above.

The potassium fluoride used may be commercially available material or spray dried to produce finely divided particles. Potassium fluoride on an inert support such as calcium fluoride may be employed but is considered uneconomical.

The ratio of potassium fluoride to chlorinated benzoyl chloride is preferably at least stoichiometric to maximize the product yield. More preferably, the molar ratio of potassium fluoride to chlorinated benzoyl chloride is about 1 to about 5, and most preferably, about 3 to about 5.

Any inert polar organic solvent may be used. Preferred solvents are amide solvents such as dimethylformamide, N-methylpyrrolidinone, sulfoxide solvents such as dimethylsulfoxide, and sulfone solvents. Most of these solvents are available in commercial quantities.

Sulfone solvents are more preferred because they are most inert toward the reactions under the operating conditions of the present process.

Of the sulfone solvents, the most preferred are aliphatic sulfones of the formula: $R_1$—$SO_2$—$R_2$ where $R_1$ and $R_2$ are the same or different and are alkyl groups of generally about 1 to 8 carbon atoms, and preferably about 1 to 4 carbon atoms or $R_1$ and $R_2$ together are alkylene units of 4 to 5 carbon atoms. Illustrative aliphatic sulfone solvents include dimethylsulfone, diethylsulfone, dipropylsulfone, dibutylsulfone, dipentylsulfone, dihexylsulfone, diheptylsulfone, dioctylsulfone, methylethylsulfone, tetramethylenesulfone, and pentamethylenesulfone. The most preferred aliphatic sulfone solvent is tetramethylenesulfone. Most of the aliphatic sulfone solvents are available in commercial quantities; otherwise, the compounds may be prepared by oxidation of the appropriate alkyl sulfide.

The amount of solvent used is preferably at least 2 times by weight the amount of the starting chlorinated benzoyl chloride, more preferably about 2 to about 25 times, and most preferably about 3 to about 7 times.

The chlorinated benzoyl chloride, potassium fluoride, and solvent are heated to a temperature sufficient to initiate the reaction. The temperature is preferably about 100° to about 250° C., more preferably about 120° to about 190° C., and most preferably about 180° to about 190° C. The time required for reaction depends upon the temperature used. The reaction time is preferably about 1 to about 10 hours, more preferably about 5 to about 10 hours, and most preferably about 8 to about 10 hours.

The fluorinated benzoyl fluoride is isolated from the reaction mixture by using a known technique such has extraction or distillation. The preferred isolation technique is distillation because it permits the solvent to be recycled without any need for additional purification. It should be understood that for the subsequent reduction of the fluorinated benzoyl chloride to the fluorinated benzaldehyde, it is unnecessary to isolate the fluorinated benzoyl fluoride from the reaction solvent. Only the inorganic salts such as potassium fluoride and potassium chloride, which are present in the reaction medium, have to be removed prior to the reduction step because they interfere with the reduction step such that lower yields result.

For step (b) of the present process, the fluorinated benzoyl fluoride of Formula (II) above is reacted with Lewis acid chloride under conditions and for a time sufficient to provide a fluorinated benzoyl chloride of the Formula (III) above.

The Lewis acid chloride is used to convert the fluorinated benzoyl fluoride to the fluorinated benzoyl chloride. Illustrative Lewis acid chlorides are aluminum chloride, phosphorus chloride, and antimony chloride. Most of these materials are available in commercial quantities. The preferred Lewis acid chloride is aluminum chloride because it is inexpensive and is highly effective in effecting this transformation without the formation of reaction by-products.

The molar ratio of Lewis acid chloride to fluorinated benzoyl fluoride is preferably less than about 1.50, more preferably about 0.3 to about 1.0, and most preferably about 0.30 to about 0.40. If greater than about 1.50 is used, side reactions occur which lower the process yield.

The fluorinated benzoyl fluoride and Lewis acid chloride are initially maintained at a temperature of preferably about −10° to about 20° C., more preferably about −5° to about 5° C., and most preferably about 0° to about 5° C. The reaction time is preferably about 0.5 to about 2 hours, and more preferably about 0.5 to about 1 hour. After this period, the conversion to the fluorinated acid chloride is about 80% complete. To complete the reaction, the mixture of fluorinated benzoyl fluoride and fluorinated benzoyl chloride and Lewis acid are heated to a temperature of preferably about 70° to about 120° C., more preferably about 80° to about 100° C., and most preferably about 85° to about 90° C. The reaction is complete in about one hour.

The fluorinated benzoyl chloride is isolated from the reaction mixture by using a known technique such as extraction or distillation. The preferred isolation technique is distillation because it permits the solvent (if one is employed) to be recycled without any need for additional purification. As mentioned earlier, it should be understood that for the subsequent reduction of the fluorinated benzoyl chloride to the fluorinated benzaldehyde, it is necessary to isolate the fluorinated benzoyl chloride from the solvent. Only the inorganic salts such as aluminum fluoride, which are present in the reaction medium, have to be removed prior to the reduction step because these salts adversely react with the reduction catalyst by lowering its activity so that lower yields result.

For step (c) of the present process, the fluorinated benzoyl chloride of Formula (III) above in solvent is then reduced with hydrogen gas in the presence of a catalyst under conditions and for a time sufficient to provide the fluorinated benzaldehyde of Formula (IV) above. Preferably, the reduction occurs with hydrogen gas in the presence of a transition metal catalyst. The transition metal catalyst is preferably palladium or platinum. Because palladium catalysts are cheaper, a palladium catalyst is more preferably used. The metal may be used alone or mixed with a carrier such as activated carbon, coke, alumina, diatomaceous earth, or barium sulfate. If a carrier is used, palladium on barium sulfate is preferred; this catalyst is commercially available and is known as the Rosenmund catalyst. The Rosenmund reduction has been reviewed in Mosettig et al., *Organic Reactions* 4, 362 (1948). The catalyst may be in the form of a powder, granules, or pellets having a diameter appropriate for practical use.

The amount of catalyst used per 1000 moles fluorinated benzoyl chloride is preferably about 0.01 to about 10 moles, more preferably about 0.01 to about 8 moles, and most preferably about 0.05 to about 5 moles.

Any solvent inert to the reduction conditions may be used. Preferred solvents include alkylarenes, hydrogenated arene, and sulfones. Illustrative alkylarene solvents include toluene, o-xylene, m-xylene, and p-xylene. Illustrative hydrogenated arenes solvents include cyclohexane and decahydronaphthalene. An illustrative sulfone solvent is tetramethylenesulfone. The more preferred solvent is decahydronaphthalene. These solvents are commercially available. The amount of solvent used is preferably about 1 to about 10 times, more preferably about 2 to about 8 times, and most preferably about 3 to about 6 times the weight of the fluorinated benzoyl chloride.

The reduction is performed by passing a dispersed steam of hydrogen gas substrate to the reactant. The reaction mixture of the fluorinated benzoyl chloride, catalyst, and solvent is heated to a temperature of preferably about 20° to about 220° C., more preferably about 80° to about 160° C., and most preferably about 100° to about 140° C. The reaction time is preferably about 1 to about 10 hours, more preferably about 2 to about 8 hours, and most preferably about 4 to about 6 hours.

The fluorinate benzaldehyde is isolated from the reaction mixture by using a known technique such as extraction is distillation. The preferred isolation technique is distillation because it permits the solvent to be recycled without any need for additional purification.

For step (d) of the present process, the fluorinated benzaldehyde of Formula (IV) above is heated in the presence of catalyst for a time sufficient to provide the fluorinated benzene of Formula (V); this step is the subject of commonly assigned U.S. patent application Ser. No. 220,869, filed July 8, 1988, which is hereby incorporated by reference. The fluorinated benzaldehyde, either neat or in a solvent inert to the decarbonylation conditions, is heated in the presence of a transition metal catalyst.

The transition metal catalyst is preferably palladium or platinum. The catalyst may or may not be the same as the catalyst used for the prior reduction. Because palladium catalysts are cheaper, a palladium catalyst is preferably used. The metal may be in various forms including colloidal or on a support such as activated carbon, barium sulfate, coke, alumina, or diatomaceous earth. The preferred catalysts are palladium or barium sulfate and palladium on activated carbon. Palladium on activated carbon is most preferred because the rate of decarbonylation is the highest.

Colloidal palladium may be prepared in any manner known in the art. As examples, the metal may be dispersed by striking an arc under water. Also, the reductive precipitation process may be controlled to yield particles of colloidal dimensions; typically, the colloidal particles have diameters in the range of about $10^2$ to $10^3$ nm. Also, metal hydroxide particles of colloidal dimensions may be precipitated and subsequently reduced.

Palladium on a support provides a means of retaining the palladium particles in a state which is both stable towards agglomeration and is accessible to the benzaldehyde compound. Palladium may be introduced to the support in any manner known in the art. As examples, palladium, from an aqueous solution or suspension, may be introduced by impregnation, adsorption or ion exchange, co-precipitation, or deposition, followed by drying and hydrogen reduction.

The amount of catalyst used per 1000 moles fluorinated benzaldehyde is preferably about 0.01 to about 10 moles, and more preferably about 0.05 to about 10 moles.

The fluorinated benzaldehyde is heated to a temperature of preferably about 140° to about 250° C., more preferably about 160° to about 220° C., and most preferably about 180° to about 200° C. The reaction time is preferably about 1 to about 10 hours, more preferably about 1 to about 6 hours, and most preferably about 2 to about 4 hours.

The fluorinated benzaldehyde and catalyst may be stirred efficiently in a reaction vessel fitted with a distillation column which separates the fluorinated benzene from the starting fluorinated benzaldehyde. Because the fluorinated benzene has a boiling point which is lower than the reaction temperature, the product may be distilled from the reaction medium. Generally, the fluorinated benzene distills as carbon monoxide is evolved; hence, no work-up procedure for solvent removal is required.

If the decarbonylation is to be performed in a solvent inert to the decarbonylation conditions, the preferred solvent is tetramethylenesulfone. Thus, it is possible to perform the entire present process in a single reaction solvent in one pot provided that the inorganic salts are removed by filtration.

Thus, the present process obviates the problems associated with the Balz-Schiemann technology. The present process provides an economical means for producing difluorobenzenes such as 1,3-difluorobenzene which is employed as a chemical intermediate in a variety of applications including pharmaceutical and agricultural.

The present invention is more fully illustrated by the following non-limiting Examples.

EXAMPLE 1

Part A

Fluorination Step 50 g (0.239 mol) of 2,4-dichlorobenzoylchloride, 62.3 g (1.07 mol) of potassium fluoride, and 250 ml (315 g) of tetramethylenesulfone were heated to 180°–190° C. After 10 hours, conversion of the starting material was complete. The product 2,4-difluorobenzoylfluoride was distilled at reduced pressure as colorless liquid. Yield: 30 g (79%); purity: 99.5%.

Part B

Conversion Step 13.5 g (.085 mol) of 2,4-diflurobenzoylfluoride were cooled to about 5° C. Aluminum chloride (3.7 g; 0.028 mol) was added slowly over about 0.5 hour. The conversion to the aroyl chloride was 80% (as determined by Gas Chromatography). The reaction was warmed to 90° C. Complete conversion of the starting material resulted. The product was distilled at reduced pressure to yield 2,4-difluorobenzoylchloride as a colorless liquid. This material was not assayed but used directly in the reduction step.

Part C

Reduction Step 30 ml (27 g) of decahydronaphthalene and 0.5 g ($2.3 \times 10^{-4}$ ml) of a catalyst of 5% palladium on a barium sulfate support were added to the flask containing the 2,4-difluorobenzoylchloride. The reaction was purged with $H_2$ for 0.25 hour, then the temperature was raised to 130° C. Hydrogen was dispersed through the system for 6 hours. The product 2,4-difluorobenzaldehyde was isolated as a colorless liquid. Yield 9.8 g (82%).

Part D

Decarbonylation Step with Barium Sulfate 10 g (0.0478 mol) of 2,4-difluorobenzaldehyde and 1 g ($4.7 \times 10^{-4}$ mol) of a catalyst of 5% palladium on a barium sulfate support were placed in a reaction flask equipped with a 10 inch Vigreaux column and a distillation head. The reaction temperature was slowly raised to 200° C. The product, 1,3-difluorobenzene, was collected at 79°–80° C. as the reaction progressed. Yield of 1,3-difluorobenzene was 6.2 g (77%). Gas Chromatographic analysis indicated 100% purity. The reaction was terminated at this point. An analysis of the pot residue indicated that the decarbonylation was incomplete. The difluorobenzaldehyde was still detected.

The overall yield of the process starting from 2,4-dichlorobenzoylchloride to the isolation of 1,3-difluorobenzene was at least 50%.

Part E

Decarbonylation Step with Carbon

Part E is presented to illustrate that the decarbonylation can be performed using palladium on carbon.

24.8 g (0.175 mol) of 2,4-difluorobenzaldehyde and 0.38 g ($1.7 \times 10^{-4}$ mol) of a catalyst of 5% palladium on a carbon support were heated as described in Part D. The yield of crude 1,3-difluorobenzene was 16.3 g (82%). The product contained a trace (<1%) of aldehyde. Overall yield of 1,3-difluorobenzene from 2,4-dichlorobenzoylchloride was 53%.

While this product was of sufficient purity to be used for most applications, an additional distillation gave 1,3-difluorobenzene which was free of aldehyde.

Having described the invention in detail and by reference to preferred embodiments thereof, it will be apparent that modifications and variations are possible without departing from the scope of the invention defined in the appended claims.

What is claimed is:

1. A process for preparing difluorobenzenes comprising the steps of:
   (a) heating a chlorinated benzoyl chloride of the Formula (I)

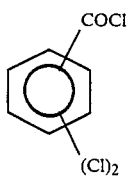

wherein each of said chlorines is independently ortho or para to said -COCl group with potassium fluoride and solvent for said chlorinated benzoyl chloride and said potassium fluoride for a time and at a temperature sufficient to provide a fluorinated benzoyl fluoride of the Formula (II)

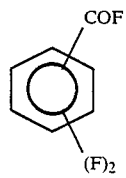

(b) reacting said fluorinated benzoyl fluoride with Lewis acid chloride under conditions and for a time sufficient to provide a fluorinated benzoyl chloride of the Formula (III)

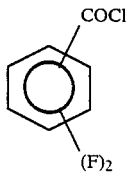

and removing inorganic salts from the reaction medium, (c) reducing said fluorinated benzoyl chloride with hydrogen gas in the presence of a catalyst under conditions and for a time sufficient to provide a fluorinated benzaldehyde of the Formula (IV)

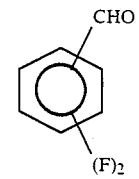

and, (d) heating said fluorinated benzaldehyde in the presence of a catalyst for a time sufficient to provide a fluorinated benzene of the Formula (V)

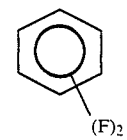

2. The process of claim 1 wherein in said step (a), said chlorinated benzoyl chloride is 2,4-dichlorobenzoylchloride.

3. The process of claim 1 wherein in said step (a), said chlorinated benzoyl chloride is 2,6-dichlorobenzoylchloride.

4. The process of claim 1 wherein in said step (a), said solvent is a sulfone.

5. The process of claim 1 wherein in said step (a), said solvent is tetramethylenesulfone.

6. The process of claim 1 wherein in said step (a), said chlorinated benzoyl chloride is heated to a temperature of about 100° to about 250° C.

7. The process of claim 6 wherein in said step (a), said chlorinated benzoyl chloride is heated for about 1 to about 10 hours.

8. The process of claim 1 wherein in said step (b), said fluorinated benzoyl fluoride is reacted with a Lewis acid chloride.

9. The process of claim 8 wherein said Lewis acid chloride is a Lewis acid chloride selected from the group consisting of aluminum chloride, phosphorous chloride, and antimony chloride.

10. The process of claim 1 wherein in said step (c), said fluorinated benzoyl chloride is reduced by hydrogen gas in the presence of a catalyst.

11. The process of claim 10 wherein said catalyst is a catalyst selected from the group consisting of platinum and palladium.

12. The process of claim 10 wherein said catalyst is mixed with a carrier selected from the group consisting of activated carbon, coke, alumina, diatomaceous earth, and barium sulfate.

13. The process of claim 1 wherein in said step (c), said fluorinated benzoyl chloride is heated to a temperature of about 20° to about 220° C.

14. The process of claim 13 wherein in said step (c), said fluorinated benzoyl chloride is heated for about 1 to about 10 hours.

15. The process of claim 1 wherein in said step (d), said catalyst is a catalyst selected from the group consisting of platinum and palladium.

16. The process of claim 15 wherein said catalyst is mixed with a carrier selected from the group consisting of activated carbon, coke, alumina, diatomaceous earth, and barium sulfate.

17. The process of claim 1 wherein in said step (d), said fluorinated benzaldehyde is heated to a temperature of about 140° to about 250° C.

18. The process of claim 17 wherein in said step (d), said fluorinated benzaldehyde is heated for about 1 to 10 hours.

19. The process of claim 1 wherein said process is performed in one solvent in one pot.

* * * * *

UNITED STATES PATENT AND TRADEMARK OFFICE
CERTIFICATE OF CORRECTION

| | |
|---|---|
| PATENT NO. | : 4,847,442 |
| DATED | : July 11, 1989 |
| INVENTOR(S) | : David Nalewajek and Michael Van Der Puy |

It is certified that error appears in the above-identified patent and that said Letters Patent is hereby corrected as shown below:

<u>Title page,</u>
After Item [19], Inventors should read -- Nalewajek et al. --

Signed and Sealed this

Thirty-first Day of August, 2004

JON W. DUDAS
*Director of the United States Patent and Trademark Office*